United States Patent [19]
Li

[11] Patent Number: 5,766,198
[45] Date of Patent: Jun. 16, 1998

[54] SURGICAL KNIFE EMPLOYING A VACUUM TO ENSURE PRECISE DEPTH OF INCISIONS

[76] Inventor: Bing Li, 1013 N. Blackwelder Ave., Edmond, Okla. 73034

[21] Appl. No.: 660,881

[22] Filed: Jun. 10, 1996

[51] Int. Cl.⁶ ............................................. A61F 09/00
[52] U.S. Cl. .................................. 606/172; 606/166
[58] Field of Search .................... 606/1, 107, 161–171, 606/172; 604/19, 22, 35

[56] References Cited

U.S. PATENT DOCUMENTS

| | | | |
|---|---|---|---|
| 4,340,059 | 7/1982 | Marinoff. | |
| 4,552,146 | 11/1985 | Jensen et al. . | |
| 4,564,637 | 1/1986 | Schachar . | |
| 4,602,630 | 7/1986 | Anis . | |
| 4,606,623 | 8/1986 | Schachar . | |
| 4,688,570 | 8/1987 | Kramer et al. | 606/172 |
| 4,705,037 | 11/1987 | Peyman et al. . | |
| 4,724,837 | 2/1988 | Gannon . | |
| 4,750,489 | 6/1988 | Berkman et al. . | |
| 4,804,364 | 2/1989 | Dieras et al. | 606/169 |
| 4,815,463 | 3/1989 | Hanna . | |
| 4,844,060 | 7/1989 | Krumeich . | |
| 5,201,747 | 4/1993 | Mastel | 606/167 |
| 5,336,236 | 8/1994 | Nevyas-Wallace | 606/166 |
| 5,405,355 | 4/1995 | Peyman et al. | 606/166 |
| 5,458,610 | 10/1995 | Feaster | 606/170 |

FOREIGN PATENT DOCUMENTS

| | | | |
|---|---|---|---|
| 203230 | 10/1983 | Germany | 606/712 |

OTHER PUBLICATIONS

Gerrit R.J. Melles, et al., "Effect of Blade Configuration, Knife Action, and Intraocular Pressure on Keratotomy Incision Depth and Shape," *Cornea*, vol. 12, No. 4, 1993, pp. 299–309.

Perry Binder, MD. "Mastel Byron Radial Keratotomy Guide," *Journal of Refractive & Corneal Surgery*, vol. 10, Nov./Dec. 1994, pp. 656–657.

Henry Gelender, M.D., et al., "Vacuum Fixation Ring for Radial Keratotomy," *Ophthalmic Surgery*, vol. 15, No. 2, Feb. 1984, pp. 126–127.

Steven R. Unterman, M.D. "Diamond Knife Corneal Incisions," *Ophthalmic Surgery*, vol. 15, No. 3, Mar. 1984, pp. 199–202.

*Primary Examiner*—Glenn K. Dawson
*Attorney, Agent, or Firm*—Hitt Chwang & Gaubes, P.C.

[57] ABSTRACT

The present invention discloses a surgical instrument system including a surgical knife for use in incising a tissue of a patient and a vacuum system coupled to the surgical knife. The surgical knife includes a blade having a cutting edge and tip associated therewith and having a width for making an incision in a tissue of a patient, and an incision depth control guard having a surface normal to the blade and at a predetermined distance above the tip of the blade. The surface of the depth control guard normal to the blade has an opening formed therein through which a vacuum is drawn to create a suction force whereby the tissue to be incised is pulled into substantial contact with the surface. The system further includes a vacuum device suitably operative to create a suction force through the opening in the surface of the incision depth control guard to thereby maintain substantial contact between the tissue to be incised and the surface of the incision depth control guard.

17 Claims, 4 Drawing Sheets

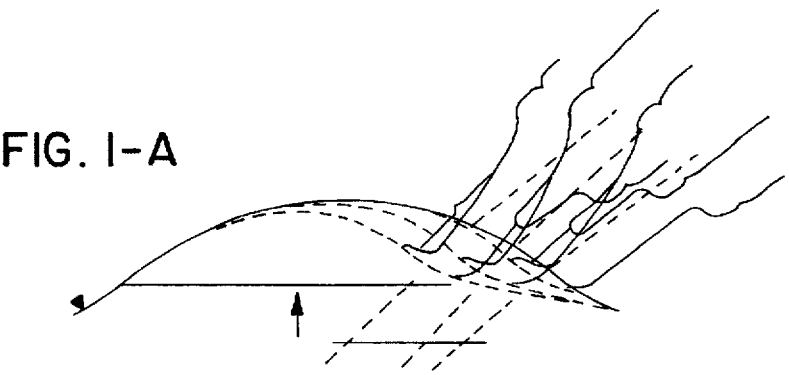
FIG. 1-A
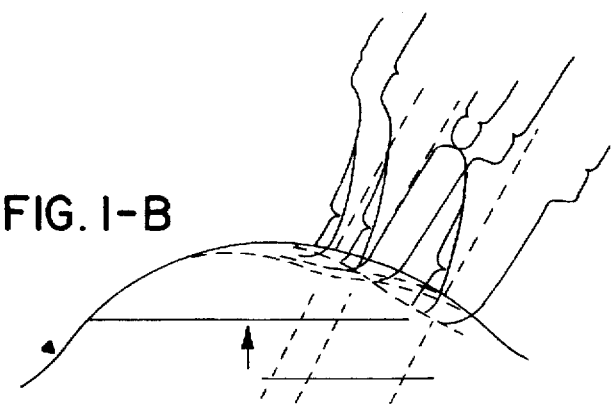
FIG. 1-B
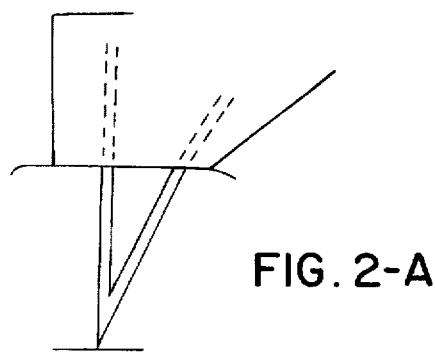
FIG. 2-A
PERPENDICULAR
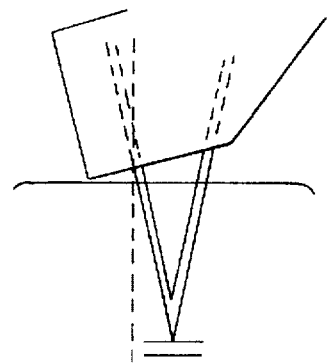
10°
FORWARD TILTING
FIG. 2-B
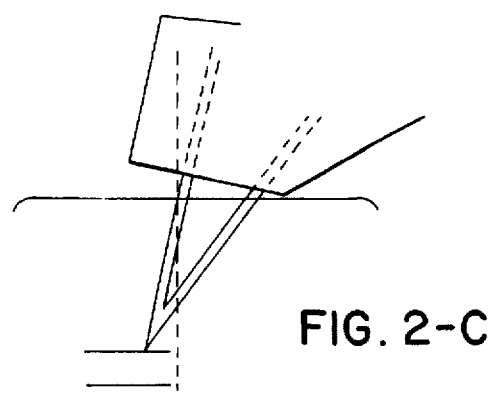
FIG. 2-C
10°
BACKWARD TILTING

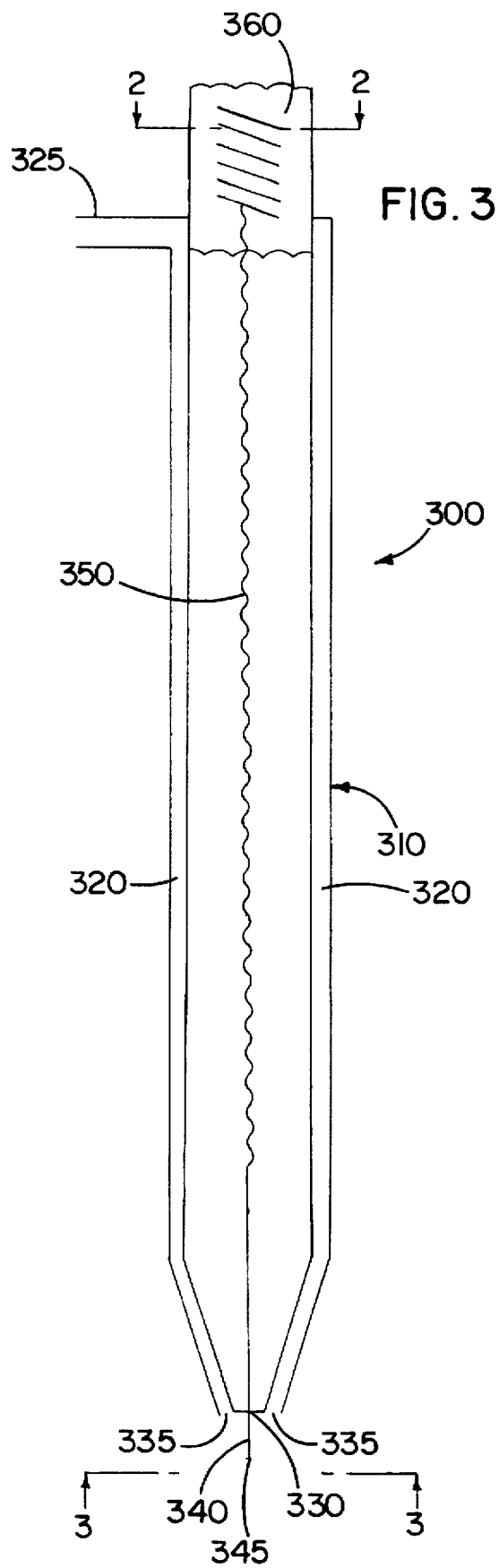
FIG. 3-A
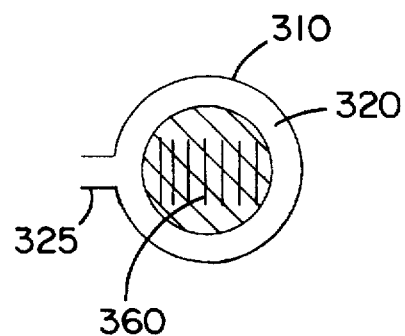
FIG. 3-B
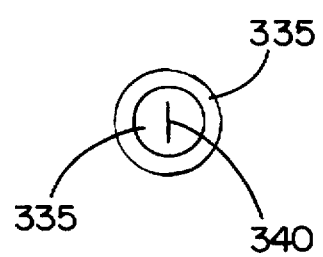
FIG. 3-C

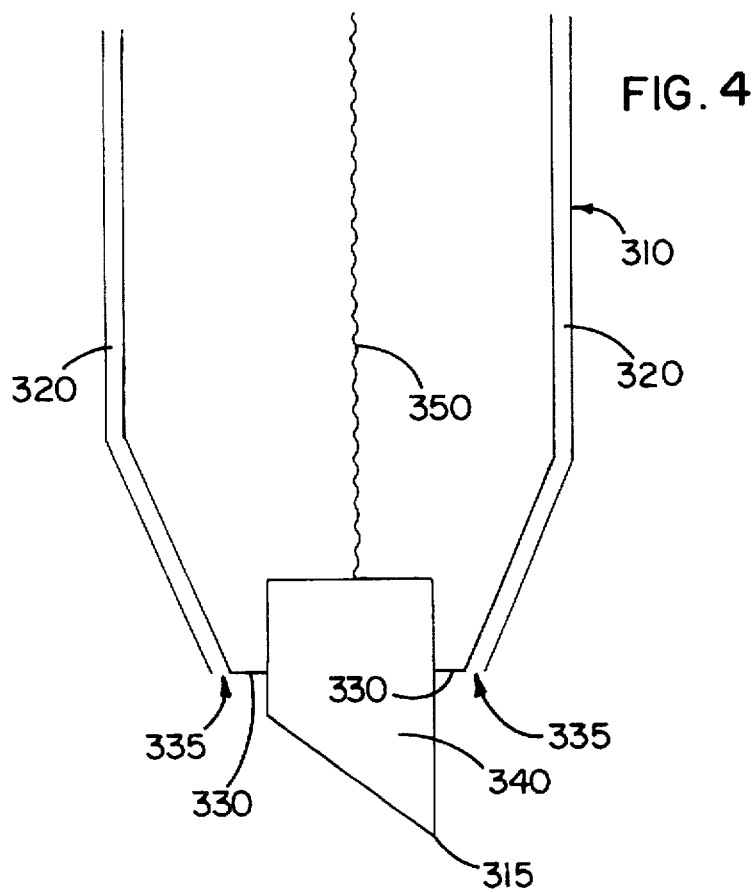
FIG. 4
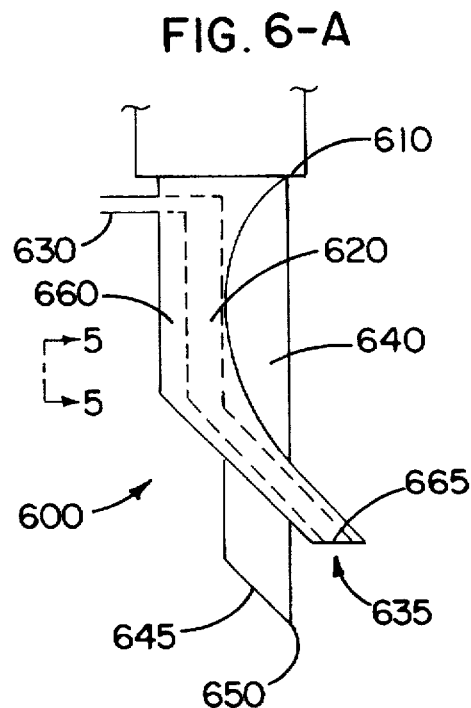
FIG. 6-A
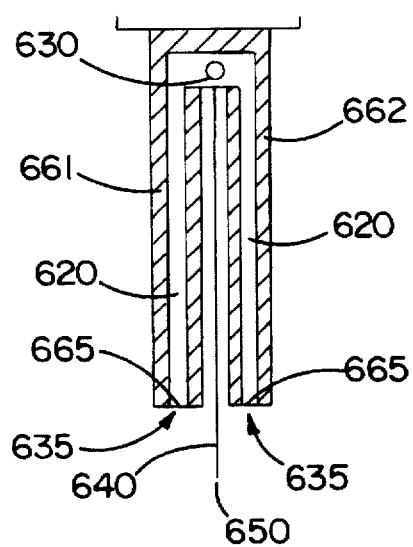
FIG. 6-B

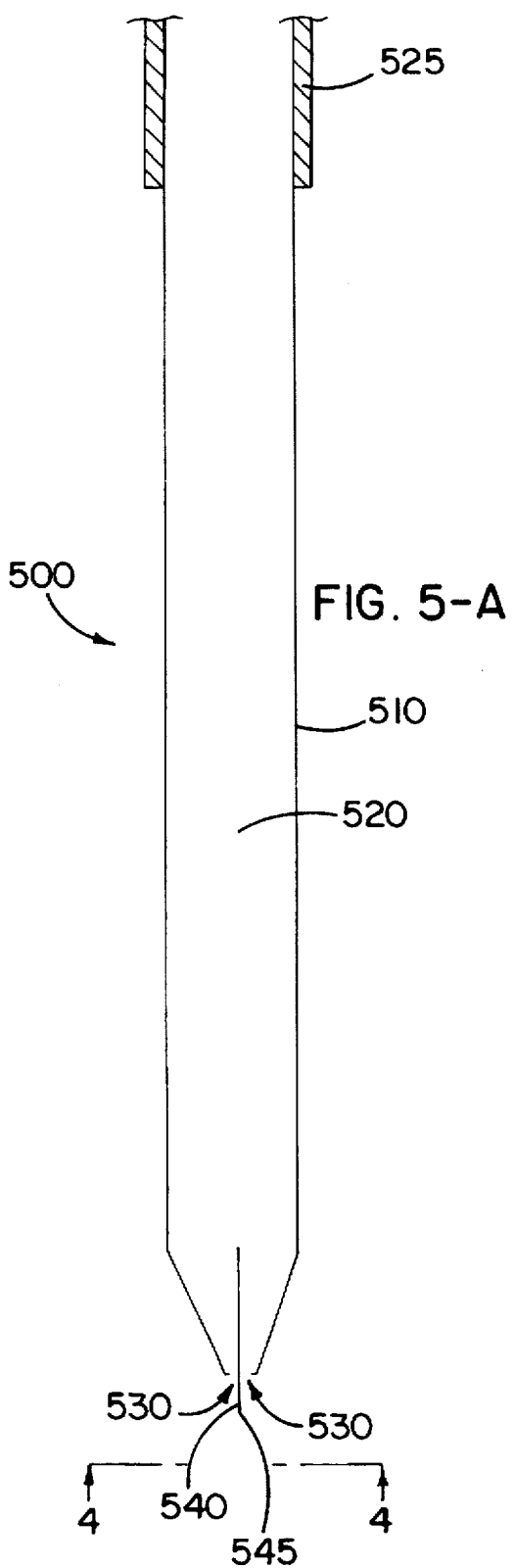
FIG. 5-A
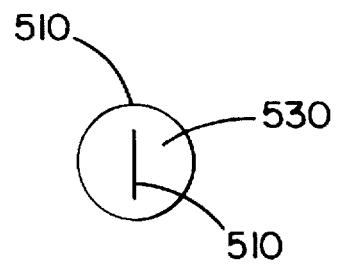
FIG. 5-B
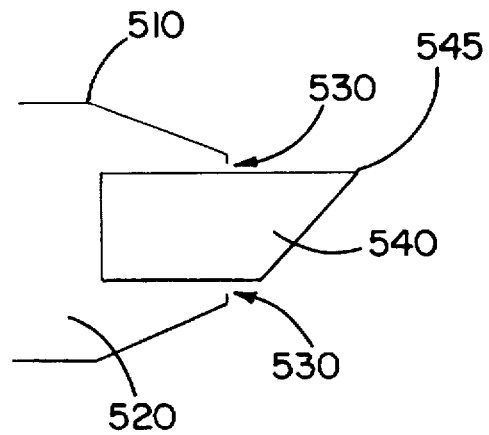
FIG. 5-C

SURGICAL KNIFE EMPLOYING A VACUUM TO ENSURE PRECISE DEPTH OF INCISIONS

TECHNICAL FIELD OF THE INVENTION

The present invention is directed, in general, to surgical instruments, and, more specifically, to a surgical knife for precision incisions.

BACKGROUND

Radial keratotomy ("RK") modifies the refractive power of the cornea and thereby reduces myopia. The surgery involves deep radial corneal incisions, with eight to sixteen incisions usually effective for moderate myopes. Presently used radial keratotomy ("RK") surgical instruments and techniques to correct low to moderate myopia generally yield positive, although slightly unpredictable, results. The lack of predictability is the most serious shortcoming of RK, and is generally attributed to a lack of precision in controlling the depth of each incision. Although most surgical knives suitable for RK are adjustable, incision depths actually realized are not predictable and depth variations of 30% or more may occur within the same incision. Thus, a means to ensure precise incision depths is desired if RK procedures are to become generally accepted as an effective cure for myopia.

To improve depth of incision consistency, an RK knife may include a footplate that is adapted to be placed against the cornea of the eye. U.S. Pat. No. 5,458,610 to Feaster, entitled "REFRACTIVE SURGERY KNIFE AND PROCESS," discloses a RK knife having a footplate and a blade that is held by a blade support member which can locate the cutting edge of the blade in the opening of the footplate and beyond for forming a radial incision in the cornea of the eye by being pressed directly into the cornea tissue. It is found, however, that decreased incision depth may result from corneal deformation by the footplates. (Gerrit R. J. Melles, et al., *J. Refract Corneal Surg.*, Vol. 12, No. 4, 1993).

Corneal tissue deformation by a RK knife footplate is illustrated in FIG. 1-A and FIG. 1-B. FIG. 1-A illustrates the relative corneal deformation caused by an uphill incision. FIG. 1-B illustrates the relative corneal deformation caused by a down incision. An examination of both figures illustrates that relatively more central deformation is seen with the uphill incision, and more peripheral deformation with the downhill incision. In both cases, however, the result of corneal deformation is variation in the achieved incision depth.

A further source of variation in achieved incision depth is longitudinal knife tilt (in the direction of the incision). This is illustrated in FIGS. 2-A, 2-B, and 2-C. With the knife properly resting on the footplates (FIG. 2-A), the blade theoretically penetrates to the desired depth. Because of corneal deformation, however, the achieved incision depth may not be the desired depth. Furthermore, the knife axis may tilt as the surgeon draws the knife across the cornea, resulting in decreased depth of incision. Because of the blade orientation to the footplates, a forward tilt of the knife creates a smaller decrease in incision depth (FIG. 2-B) than when the knife is tilted backward (FIG. 2-C). To compensate for variations in achieved incision depth due to knife tilt, surgeons typically adjust the blade extension as appropriate for the particular technique used.

An incision depth of 90% of the corneal thickness is considered desirable as a compromise between maximizing the reduction of myopia and minimizing the risk of microperforation of the cornea. To achieve sufficient depth using "downhill" incisions with the oblique blade edge, surgeons typically extend their blades up to 120% of the thinnest corneal pachometry readings. Downhill incisions are also referred to as centrifugal optical clear zone to limbus, in-to-out, and "American technique." Alternatively, a surgeon may use an "uphill" incision, with a blade setting of 80–100% of the thinnest corneal pachometry reading, using the perpendicular blade edge. Uphill incisions are also known as centripetal limbus to optical clear zone, out-to-in, and "Russian technique." Neither the "American" and "Russian" techniques, however, ensure precise incision depths within the same incision.

Using current RK knives, the cutting resistance of the corneal tissue also results in variations in incision depth. The resistance to cutting results in corneal deformation by the "wing," "reversed wing," and "plough" effects known to those skilled in the art. In theory, the resistance force of the corneal tissue to the blade has an upward vector that tends to lift the blade out of the tissue (wing effect). The upward force on the blade may also result in a downward force on the eye tissue by the blade, causing the tissue to protrude into the anterior chamber (reversed wing effect), or cause the blade to dig deeper into the stromal tissue (plough effect).

Accordingly, what is needed in the art is an ophthalmic surgical knife for precision incisions.

SUMMARY

To address the above-discussed deficiencies of the prior art, the present invention provides an ophthalmic surgical instrument for use in incising a cornea of a patient. The opthalmic surgical instrument employs a vacuum for ensuring precise depth of incision.

In a preferred embodiment, the ophthalmic surgical instrument includes a surgical blade having a cutting edge and tip associated therewith and having a suitable width for making an incision in the cornea of a patient, and an elongated handle with a hollow space formed therein and through which a vacuum is used to create a suction force at an opening in the elongated handle at a planar surface above the tip of the surgical blade. The suction forces created at the planar surface are sufficient to draw the surface of the cornea, without substantial change in the curvature thereof into substantial contact with the planar surface. The contact between the surface of the cornea and the planar surface is maintained as the surgeon draws the knife across the cornea, thereby ensuring a precise depth of incision.

In a preferred embodiment, the length of the blade of the surgical instrument is fixed in place and has a dimension from the planar surface to the tip of the blade that corresponds to a desired incision depth.

In a preferred embodiment, the surgical blade of the ophthalmic surgical instrument is a diamond edge steel blade. The elongated handle of the ophthalmic surgical instrument is preferably constructed from a transparent plastic material whereby the surgeon's vision of the surgical blade is not occluded by the handle.

In an alternate preferred embodiment, the ophthalmic surgical instrument includes a surgical blade having a cutting edge and tip associated therewith and having a suitable width for making an incision in the cornea of a patient, and an elongated handle with a double wall construction having a hollow space formed therein and through which a vacuum is used to create a suction force at an opening in the elongated handle at a planar surface above the tip of the surgical blade.

In another preferred embodiment, the ophthalmic surgical instrument includes a surgical blade having a cutting edge and tip associated therewith and having a suitable width for making an incision in the cornea of a patient, an elongated handle, and a footplate secured to the elongated handle and through which the surgical blade extends. The footplate has a hollow space formed therein and through which a vacuum is drawn to create a suction force at an opening in the footplate at a planar surface above the tip of the surgical blade.

In alternate embodiments, the ophthalmic surgical instrument may further include a blade extension mechanism operative to precisely adjust a distance of extension of the tip of the surgical blade from the planar surface, the distance of extension of the blade corresponding to a desired incision depth.

The present invention further discloses an ophthahnic surgical instrument system including an ophthalmic surgical knife for use in incising a cornea of a patient, and a vacuum device associated therewith. The ophthalmic surgical knife includes a surgical blade having a cutting edge and tip associated therewith and having a suitable width for making an incision in the cornea of a patient, and an elongated handle having a hollow space formed therein for directing a vacuum to a planar surface above the tip of the surgical blade, the planar surface having at least one opening associated therewith. The vacuum device is coupled to the ophthalmic surgical knife and is suitably operative to create a suction force through the at least one opening associated with the planar surface above the tip of the surgical blade. The suction force is adjusted to maintain substantial contact between a surface of a cornea and the planar surface. The contact between the cornea surface and the planar surface is maintained as the surgeon draws the knife across the cornea, thereby ensuring a precise depth of incision.

The foregoing has outlined, rather broadly, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention, and that the surgical instrument of the present invention may be used to advantage in surgical procedures other than radial keratotomy. Those skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following descriptions taken in conjunction with the accompanying drawings, in which:

FIG. 1-A illustrates the relative corneal deformation caused by an uphill incision;

FIG. 1-B illustrates the relative corneal deformation caused by a downhill incision;

FIG. 2-A illustrates the relative incision depth with no longitudinal knife tilt (in the direction of the incision);

FIG. 2-B illustrates the relative incision depth with forward tilting longitudinal knife tilt (in the direction of the incision);

FIG. 2-C illustrates the relative incision depth with backward tilting longitudinal knife tilt (in the direction of the incision);

FIG. 3-A is a partial cross-sectional view of a preferred embodiment of an RK knife in accordance with the principles of the present invention;

FIG. 3-B is a view of FIG. 3-A taken along lines 2—2 thereof;

FIG. 3-C is a view of FIG. 3-A taken along lines 3—3 thereof;

FIG. 4 illustrates a second cross-sectional view of a preferred embodiment of the RK knife of FIG. 3;

FIG. 5-A is a partial cross-sectional view of a second preferred embodiment of an RK knife in accordance with the principles of the present invention;

FIG. 5-B is a view of FIG. 5-A taken along lines 4—4 thereof;

FIG. 5-C illustrates a second cross-sectional view of the RK knife of FIG. 5-A;

FIG. 6-A is a partial cross-sectional view of a third preferred embodiment of an RK knife in accordance with the principles of the present invention; and FIG. 6-B is a view of FIG. 6-A taken along lines 5—5 thereof

DETAILED DESCRIPTION

In order to overcome the disadvantages associated with prior art RK knives, the following detailed description discloses preferred embodiments of a modified conventional RK knife including a vacuum system that is used to maintain the RK kinife in substantial contact with the surface of the cornea, thereby enabling a surgeon to achieve a more precise depth of incision. The present invention recognizes that as the surgeon draws the knife blade across the eye he must apply downward pressure in order to overcome the cutting resistance of the eye tissue, causing the local cornea to deform. The deformation causes variations in the incision depth over the length of the incision. The present invention obviates the need for the surgeon to apply downward pressure as the incision is made. This is accomplished by employing a vacuum system to draw the corneal surface into substantial contact with a surface above the blade tip. The surface is at a predetermined precise distance from the tip of the knife blade. Therefore, as the surgeon draws the knife across the corneal surface, precise incision depth is maintained.

Referring now to the drawings, FIG. 3-A is a partial cross-sectional view of a preferred embodiment of an RK knife 300 in accordance with the principles of the present invention. The knife 300 comprises an elongated cylindrical handle 310 having a double wall construction such that a hollow space 320 is formed therein. The hollow space 320 extends to the blade end of the knife, terminating at an opening 335. A vacuum fitting 325 is coupled to the handle 310 and is suitably designed to connect to a vacuum system (not shown) such that a suction force is obtained by drawing a vacuum through opening 335.

The handle 310 has a base 330 through which a blade 340 extends. Blade 340 is coupled to a blade extension system comprising connecting member 350 and a blade extension mechanism 360. The blade extension mechanism 360 and connecting member 350 are suitably operative to extend the tip 345 ofblade 340 a precise distance through the base 330 of handle 310. Those of skill in the art will readily appreciate the various mechanisms suitably operative to function as a blade extension mechanism, including, but not limited to, precision caliper-type mechanisms. In alternate embodiments of RK knife 300, the length of the blade is fixed and has a dimension from the planar surface to the tip of the blade that corresponds to a desired incision depth.

FIG. 3-B is a view of FIG. 3-A taken along lines 2—2 thereof As is illustrated, the hollow space 320 is formed within the double wall construction of handle 310 and has a path through vacuum fitting 325 to a vacuum system (not shown).

FIG. 3-C is a view of FIG. 3-A taken along lines 3—3 thereof Blade 340 extends through base 335 of handle 310, and is circumscribed by opening 335.

FIG. 4 illustrates a second cross-sectional view of a preferred embodiment of the RK knife of FIG. 3. In use, a surgeon will extend blade 340, using the blade extension system comprising connecting member 350 and blade extension mechanism 360, until the tip 345 is the precise distance from base 330 corresponding to a desired incision depth. By suction forces created around the base 330 of handle 310 through openings 335, the surface of the cornea is drawn into substantial contact with base 330. The contact between the cornea surface and base 330 is maintained as the surgeon draws the knife across the surface, thereby ensuring a precise depth of incision.

FIG. 5-A is a partial cross-sectional view of another preferred embodiment of an RK knife in accordance with the principles of the present invention. The knife 500 comprises an elongated cylindrical handle 510 having a hollow space 520 formed therein. The cylindrical handle 510 is preferably tapered at the blade end. The hollow space 520 extends to the blade end of the knife, terminating at an opening 530. A vacuum tube 525 is coupled to the handle 510 at the end opposite the blade 540, and is suitably designed to connect to a vacuum system (not shown) such that a suction force is created by drawing a vacuum through opening 530.

The handle 510 has an opening 530 through which a blade 540 extends. Blade 540 is fixed in place and has a dimension from the plane comprising opening 530 to the tip 545 of blade 540 that corresponds to a desired incision depth. Typical desired incision depths include, without limitation, 0.54, 0.56, 0.60, 0.70, or 0.75 millimeters. In alternate embodiments, blade 540 is coupled to a blade extension system, as described with reference to RK knife 300, supra. The handle 510 is preferably fabricated from a transparent plastic material whereby a surgeon's vision of the blade is not occluded by handle 510.

FIG. 5-B is a view of FIG. 5-A taken along lines 4—4 thereof Blade 540 extends through and is circumscribed by opening 530 of handle 510.

FIG. 5-C illustrates a second cross-sectional view of the RK knife of FIG. 5-A. In use, a surgeon will select a RK knife having a precise distance between tip 545 and the plane comprising opening 530 corresponding to a desired incision depth. By suction forces created through the opening 530 of handle 510, the surface of the cornea is drawn into substantial contact with the planar surface formed bathe opening 530. The contact between the corneal surface and the base of handle 510 surrounding opening 530 is maintained as the surgeon draws the knife across the surface, thereby ensuring a precise depth of incision.

FIG. 6-A is a partial cross-sectional view of a third preferred embodiment of an RK knife in accordance with the principles of the present invention. The knife 600 comprises an elongated handle 610 suitably adapted to secure a surgical blade 640 having a cutting edge 645 and a tip 650. To the end of handle 610 at which blade 640 is secured is also attached a depth gauge 660. The depth gauge 660 is comprised of two legs extending on either side of blade 640 and terminating at a flat surface 665 above the tip 650 of blade 640. Formed within each leg of depth gauge 660 is a hollow space 620 that extends from a vacuum fitting 630 to the flat surface 665, terminating at an opening 635. A vacuum tube (not shown) is suitably coupled to the vacuum fitting 630, and is suitably designed to connect to a vacuum system (not shown) such that a suction force is created by drawing a vacuum through opening 635. Blade 640 is either fixed in place or may be extendable such that a dimension from the plane comprising flat surface 665 to the tip 650 of blade 640 corresponds to a desired incision depth.

FIG. 6-B is a view of FIG. 6-A taken along lines 5—5 thereof Blade 640 extends between legs 661, 662 of depth gauge 660. A vacuum fitting 630 is suitably designed to couple a vacuum system (not shown) to a hollow space 620 formed within legs 661, 662 that extends to a flat surface 665, terminating at an opening 635. In use, a surgeon will select a RK knife having a precise distance between tip 650 and the plane comprising flat surface 665 corresponding to a desired incision depth. By suction forces created through the openings 635 of depth gauge 660, the surface of the cornea is drawn into substantial contact with the flat surface 665 at openings 635. The contact between the corneal surface and the flat surface 665 at openings 635 is maintained as the surgeon draws the knife across the surface, thereby ensuring a precise depth of incision.

From the foregoing detailed description, those of skill in the art will appreciate the advantages that can be derived from the ophthalmic surgical knife employing a vacuum means to ensure precise depth of incisions. Furthermore, although the present invention is described with reference to radial keratotomy surgical procedures, it is recognized that the present invention may also be employed to advantage in other surgical procedures including, without limitation, astigmatism correction and relaxing incisions following penetrating keratoplasty. It should be further noted that the drawings are not drawn to scale and that those skilled in the art should understand that they can make various changes, substitutions and alterations herein without departing from the spirit and scope of the invention in its broadest form.

What is claimed is:

1. A surgical knife for use in incising a tissue of a patient, said surgical knife comprising:

a guiding portion;

a blade, having a cutting edge and a tip, for making an incision in said tissue of said patient, an end of said blade distal from said tip coupled to said guiding portion;

an incision depth control guard, coupled to said guiding portion, having a surface substantially normal to said blade and at a predetermined distance from said tip of said blade, said surface having an opening formed therein through which a vacuum is drawn to create a suction force whereby said tissue is pulled into substantial contact with said surface; and a blade extension mechanism, coupled to said blade, operative to precisely adjust said predetermined distance of said surface of said incision depth control guard from said tip of said blade, said predetermined distance corresponding to a desired incision depth.

2. The surgical knife of claim 1 wherein said surface of said incision depth control guard is substantially planar.

3. The surgical knife of claim 1 wherein said guiding portion comprises an elongated handle.

4. The surgical knife of claim 3 wherein said surface of said incision depth control guard is an end of said elongated handle proximate said blade.

5. The surgical knife of claim 3 wherein said elongated handle has a hollow space formed therein and through which said vacuum is directed to said opening in said surface.

6. A surgical instrument system comprising:
- a surgical knife for use in incising a tissue of a patient, said surgical knife comprising:
  - a guiding portion;
  - a blade, having a cutting edge and a tip, for making an incision in said tissue of said patient, an end of said blade distal from said tip coupled to said guiding portion;
  - an incision depth control guard, coupled to said guiding portion, having a surface substantially normal to said blade and at a predetermined distance from said tip of said blade, said surface having an opening formed therein through which a vacuum is drawn to create a suction force whereby said tissue is pulled into substantial contact with said surface; and
  - a blade extension mechanism, coupled to said blade, operative to precisely adjust said predetermined distance of said surface of said incision depth control guard from said tip of said blade, said predetermined distance corresponding to a desired incision depth; and
- a vacuum device coupled to said surgical knife and suitably operative to create a suction force through said opening to maintain substantial contact between said tissue and said surface.

7. The surgical instrument system of claim 6 wherein said surface of said incision depth control guard is substantially planar.

8. The surgical instrument system of claim 6 wherein said guiding portion comprises an elongated handle.

9. The surgical instrument system of claim 8 wherein said surface of said incision depth control guard is an end of said elongated handle proximate said blade.

10. The surgical instrument system of claim 8 wherein said elongated handle has a hollow space formed therein and through which said vacuum is directed to said opening in said surface.

11. A surgical knife for use in incising a tissue of a patient, said surgical knife comprising:
- a guiding portion;
- a blade, having a cutting edge and a tip, for making an incision in said tissue of said patient, an end of said blade distal from said tip coupled to said guiding portion; and
- a footplate, coupled to said guiding portion, sand footplate having an elongated opening formed therein through which said blade extends and a surface substantially normal to said blade and at a predetermined distance from said tip of said blade, said surface having an opening formed therein through which a vacuum is drawn to create a suction force whereby said tissue is pulled into substantial contact with said surface.

12. The surgical knife of claim 11 wherein said surface of said footplate is substantially planar.

13. The surgical knife of claim 11 wherein said guiding portion comprises an elongated handle.

14. A surgical instrument system comprising:
- a surgical knife for use in incising a tissue of a patient, said surgical knife comprising:
  - a guiding portion;
  - a blade, having a cutting edge and a tip, for making an incision in said tissue of said patient, an end of said blade distal from said tip coupled to said guiding portion; and
  - a footplate, coupled to said guiding portion, sand footplate having an elongated opening formed therein through which said blade extends and a surface substantially normal to said blade and at a predetermined distance from said tip of said blade, said surface having an opening formed therein through which a vacuum is drawn to create a suction force whereby said tissue is pulled into substantial contact with said surface; and
- a vacuum device coupled to said surgical knife and suitably operative to create a suction force through said opening to maintain substantial contact between said tissue and said surface.

15. The surgical instrument system of claim 14 wherein said surface of said footplate is substantially planar.

16. The surgical instrument system of claim 14 wherein said guiding portion comprises an elongated handle.

17. A method for use in incising a tissue, said method comprising the steps of:
- inserting a blade into said tissue, said blade having a cutting edge and a tip, an end of said blade distal from said tip coupled to a guiding device;
- drawing a vacuum through an incision depth control guard, coupled to said guiding device, said incision depth control guard having a bottom surface substantially normal to said blade at a predetermined distance from said tip, said predetermined distance being substantially equal to the desired depth of an incision, said bottom surface having an opening formed therein through which said vacuum can be drawn to create a suction force sufficient to cause the upper surface of said tissue proximate said blade to be drawn into substantial contact with said bottom surface of said incision depth control guard; and
- applying a force to said guiding device to cause said cutting edge of said blade to incise said tissue, said vacuum holding said upper surface of said tissue in substantial contact with said bottom surface of said incision depth control guard as said blade incises said tissue, whereby said tip of said blade is maintained at said desired depth.

* * * * *